(12) United States Patent
Kang et al.

(10) Patent No.: US 9,429,537 B2
(45) Date of Patent: Aug. 30, 2016

(54) METHOD OF DETECTING VOLATILE ORGANIC COMPOUNDS

(75) Inventors: Myungchan Kang, Woodbury, MN (US); Michael C. Palazzotto, Woodbury, MN (US); Stefan H. Gryska, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 126 days.

(21) Appl. No.: 14/007,230

(22) PCT Filed: Apr. 2, 2012

(86) PCT No.: PCT/US2012/031798
§ 371 (c)(1),
(2), (4) Date: Sep. 24, 2013

(87) PCT Pub. No.: WO2012/141925
PCT Pub. Date: Oct. 18, 2012

(65) Prior Publication Data
US 2014/0021967 A1    Jan. 23, 2014

Related U.S. Application Data

(60) Provisional application No. 61/475,000, filed on Apr. 13, 2011.

(51) Int. Cl.
*G01R 27/26* (2006.01)
*G01N 27/22* (2006.01)
(Continued)

(52) U.S. Cl.
CPC ............ *G01N 27/22* (2013.01); *G01N 21/783* (2013.01); *G01N 21/8422* (2013.01);
(Continued)

(58) Field of Classification Search
CPC ............... H01L 21/00; H01L 2221/00; H01L 2223/00; H01L 2924/00; H01L 2925/00; G01N 1/00; G01N 2201/00; G01N 2203/00; C08L 89/00; C08J 3/00
See application file for complete search history.

(56) References Cited

U.S. PATENT DOCUMENTS 4,638,443 A   1/1987  Kaneyasu
4,703,646 A   11/1987 Muller
(Continued)

FOREIGN PATENT DOCUMENTS

CN    1685225 A    10/2005
CN    1802562 A    7/2006
(Continued)

OTHER PUBLICATIONS

Budd, "Polymers of intrinsic microporosity (PIMs): robust, solution-processable, organic nanoporous materials", Chemical Communications, 2004, pp. 230-231.
(Continued)

*Primary Examiner* — Huy Q Phan
*Assistant Examiner* — Temilade Rhodes-Vivour
(74) *Attorney, Agent, or Firm* — Yufeng Dong; Bradford Wright

(57) ABSTRACT

A method of using a sensor element includes: exposing a sensor element to an unknown analyte vapor; measuring a capacitance of the sensor element to obtain a measured capacitance; obtaining a true capacitance of the sensor element; exposing the semi-reflective conductive electrode to incident light and observing reflected light in order to measure a spectral change between the incident light and the reflected light; comparing the true capacitance and the measured spectral change, or at least one derivative thereof, to a reference library, the reference library comprising reference correlations between spectral change and true capacitance, or at least one derivative thereof, for a plurality of reference analyte vapors; and determining at least one of the chemical class or identity of the analyte vapor.

7 Claims, 2 Drawing Sheets

(51) Int. Cl.
  *G01N 21/78*  (2006.01)
  *G01N 33/00*  (2006.01)
  *G01N 21/84*  (2006.01)
  *C08L 89/00*  (2006.01)
  *H01L 21/00*  (2006.01)
  *G01N 21/77*  (2006.01)

(52) U.S. Cl.
  CPC ....... *G01N 27/227* (2013.01); *G01N 33/0047* (2013.01); *C08L 89/00* (2013.01); *G01N 2021/7773* (2013.01); *G01N 2021/8438* (2013.01); *H01L 21/00* (2013.01); *H01L 2223/00* (2013.01)

(56) References Cited

U.S. PATENT DOCUMENTS

| | | | |
|---|---|---|---|
| 4,975,249 A | 12/1990 | Elliott | |
| 5,269,175 A | 12/1993 | Chmiel | |
| 5,296,819 A | 3/1994 | Kuroiwa | |
| 5,511,418 A | 4/1996 | Antikainen | |
| 5,709,792 A | 1/1998 | Zdanevitch | |
| 5,777,206 A | 7/1998 | Zuchner | |
| 5,801,828 A * | 9/1998 | Collins | G01N 21/645 250/461.1 |
| 5,987,963 A | 11/1999 | Stormbom | |
| 6,165,347 A | 12/2000 | Warburton | |
| 6,187,248 B1 * | 2/2001 | O'Neill et al. | 264/425 |
| 6,320,388 B1 | 11/2001 | Sun | |
| 6,338,266 B1 | 1/2002 | Warburton | |
| 6,356,087 B1 | 3/2002 | Wallrafen | |
| 6,435,003 B1 | 8/2002 | Warburton | |
| 6,455,319 B1 | 9/2002 | Lewis | |
| 6,471,838 B1 | 10/2002 | Igel | |
| 6,571,603 B1 | 6/2003 | Doleman | |
| 6,596,236 B2 | 7/2003 | DiMeo | |
| 6,640,626 B2 | 11/2003 | Saikalis | |
| 6,691,582 B1 | 2/2004 | Nawa | |
| 6,787,047 B1 | 9/2004 | Hahn | |
| 6,815,211 B1 | 11/2004 | Blazewicz | |
| 6,895,338 B2 | 5/2005 | Hsiung | |
| 6,921,883 B2 | 7/2005 | Kato | |
| 7,160,690 B2 | 1/2007 | Orser | |
| 7,200,495 B2 | 4/2007 | Desai | |
| 7,228,725 B2 | 6/2007 | Salter | |
| 7,323,343 B2 | 1/2008 | Cox | |
| 7,449,146 B2 | 11/2008 | Rakow | |
| 7,556,774 B2 | 7/2009 | Rakow | |
| 7,680,607 B1 | 3/2010 | Smulko | |
| 7,767,143 B2 | 8/2010 | Wendland | |
| 7,816,681 B2 | 10/2010 | Moon | |
| 7,906,233 B2 | 3/2011 | Wang | |
| 2002/0098119 A1 | 7/2002 | Goodman | |
| 2002/0142478 A1 | 10/2002 | Wado | |
| 2003/0020494 A1 | 1/2003 | Desmier | |
| 2003/0166296 A1 | 9/2003 | Morrison | |
| 2003/0235817 A1 | 12/2003 | Bartkowiak | |
| 2004/0062682 A1 | 4/2004 | Rakow | |
| 2005/0014179 A1 | 1/2005 | Karlsson | |
| 2005/0045493 A1 | 3/2005 | Mahurin | |
| 2005/0100475 A1 | 5/2005 | Centanni | |
| 2005/0110138 A1 * | 5/2005 | Dutta | 257/735 |
| 2005/0140975 A1 * | 6/2005 | Sakai | G01B 11/0625 356/369 |
| 2005/0148003 A1 | 7/2005 | Keith | |
| 2006/0078960 A1 | 4/2006 | Hunter | |
| 2006/0246273 A1 | 11/2006 | McKeown | |
| 2006/0249402 A1 | 11/2006 | Snow | |
| 2007/0060811 A1 | 3/2007 | Roberts | |
| 2007/0118027 A1 | 5/2007 | Baker | |
| 2007/0140907 A1 | 6/2007 | Rakow | |
| 2007/0141580 A1 | 6/2007 | David | |
| 2007/0177130 A1 | 8/2007 | MacIntyre | |
| 2007/0190637 A1 | 8/2007 | Samsoondar | |
| 2007/0299617 A1 | 12/2007 | Willis | |
| 2008/0063575 A1 | 3/2008 | Rakow | |
| 2008/0086273 A1 | 4/2008 | Shults | |
| 2008/0137066 A1 | 6/2008 | Weinstein | |
| 2008/0270039 A1 | 10/2008 | Dunn | |
| 2008/0288182 A1 | 11/2008 | Cline | |
| 2008/0291456 A1 * | 11/2008 | Ghislain | G01N 29/022 356/450 |
| 2008/0304068 A1 * | 12/2008 | Urisu | B82Y 15/00 356/440 |
| 2008/0312859 A1 | 12/2008 | Skyggebjerg | |
| 2009/0018426 A1 | 1/2009 | Markle | |
| 2009/0058567 A1 * | 3/2009 | Dutta | 333/238 |
| 2009/0076360 A1 | 3/2009 | Brister | |
| 2009/0112478 A1 | 4/2009 | Mueller, Jr. | |
| 2009/0126460 A1 | 5/2009 | Gardner | |
| 2009/0192745 A1 | 7/2009 | Kamath | |
| 2009/0261366 A1 * | 10/2009 | Eisert | H01L 33/46 257/98 |
| 2009/0283421 A1 | 11/2009 | Farangis | |
| 2010/0093096 A1 * | 4/2010 | Acharya | B82Y 30/00 436/4 |
| 2010/0189600 A1 | 7/2010 | Hulteen | |
| 2010/0277740 A1 * | 11/2010 | Hulteen | G01N 21/274 356/445 |
| 2010/0325073 A1 | 12/2010 | Haick | |
| 2011/0031983 A1 | 2/2011 | David | |
| 2011/0045601 A1 | 2/2011 | Gryska | |
| 2013/0088244 A1 | 4/2013 | Gryska | |
| 2013/0186177 A1 | 7/2013 | Palazzotto | |
| 2013/0229194 A1 | 9/2013 | Palazzotto | |

FOREIGN PATENT DOCUMENTS

| | | |
|---|---|---|
| DE | 10041921 | 3/2002 |
| EP | 1030174 | 8/2000 |
| EP | 2009432 | 12/2008 |
| JP | 6-281610 | 10/1994 |
| WO | WO 99-08105 | 2/1999 |
| WO | WO 99-29230 | 6/1999 |
| WO | WO 01-01121 | 1/2001 |
| WO | WO 01-81890 | 11/2001 |
| WO | WO 02-39103 | 5/2002 |
| WO | WO 03-029800 | 4/2003 |
| WO | WO 03-063699 | 8/2003 |
| WO | WO 2005/001413 A2 | 1/2005 |
| WO | WO 2005-012397 | 2/2005 |
| WO | WO 2006-099518 | 9/2006 |
| WO | WO 2007-009268 | 1/2007 |
| WO | WO 2007-029033 | 3/2007 |
| WO | WO 2008-002743 | 1/2008 |
| WO | WO 2008-077745 | 7/2008 |
| WO | WO 2009-001065 | 12/2008 |
| WO | WO 2009-001070 | 12/2008 |
| WO | WO 2009-045733 | 4/2009 |
| WO | WO 2009-046011 | 4/2009 |
| WO | WO 2009-053981 | 4/2009 |
| WO | WO 2010-075333 | 7/2010 |
| WO | WO 2010-088088 | 8/2010 |
| WO | WO 2010-117599 | 10/2010 |
| WO | WO 2010-135413 | 11/2010 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-170248 | 12/2012 |
| WO | WO 2012-174099 | 12/2012 |
| WO | WO 2013-090188 | 6/2013 |

OTHER PUBLICATIONS

Budd, "Free volume and intrinsic microporosity in polymers", J. Mater. Chem., 2005, vol. 15, pp. 1977-1986.

Budd, "Solution-Processed, Organophilic Membrane Derived from a Polymer of Intrinsic Microporosity", Advanced Materials, Mar. 2004, vol. 16, No. 5, pp. 456-459.

Carta, "Novel Spirobisindanes for use as precursors to polymers of intrinsic microporosity", Organic Letters, 2008, vol. 10, No. 13, pp. 2641-2643.

(56) References Cited

OTHER PUBLICATIONS

Dai, "A capacitive humidity sensor integrated with micro heater and ring oscillator circuit fabricated by CMOS-MEMS technique", Sensors and Actuators B Chemical, 2007, vol. 122, pp. 375-380.

Endres, "A gas sensor system with dielectric and mass sensors", Sensors and Actuators B Chemical, Jan. 1992, vol. 6, No. 1-3, pp. 285-288.

Furjes, "Porous silicon-based humidity sensor with interdigital electrodes and internal heaters", Sensors and Actuators B Chemical, Oct. 2003, vol. 95, No. 1-3, pp. 140-144.

Ghanem, "High-Performance Membranes from Polyimides with Intrinsic Microporosity", Adv. Mater., Jul. 17 2008, vol. 20, No. 14, pp. 2766-2771.

Ghanem, "Polymers of Intrinsic Microporosity Derived from Bis(phenazyl) Monomers", Macromolecules, 2008, vol. 41, No. 5, pp. 1640-1646.

Matsuguchi, "Capacitive-Type Humidity Sensors Using Polymerized Vinyl Carboxylate", J. Electrochemical Soc., Mar. 1994, vol. 141, No. 3, pp. 614-618.

McKeown, "Polymers of Intrinsic Microporosity (PIMs): Bridging the Void between Microporous and Polymeric Materials", Chem. Eur. J., 2005, vol. 11, No. 9, pp. 2610-2620.

Patel, "Chemicapacitive Microsensors for Volatile Organic Compound Detection", Sensors and Actuators B Chemical, Dec. 1, 2003, vol. 96, No. 3, pp. 541-553. XP004475577.

Smiths Detection, The Cyranose 320 E Nose User's Manual Nov. 6001, Edition 5, 2000, 102 pages.

International Search Report for PCT International Application No. PCT/US2012/031798, Mailed on Jun. 28, 2012, 4 pages.

Co-pending U.S. Appl. No. 14/007,144 entitled "Electronic Device Including Calibration Information and Method of Using the Same", Pallazzotto et al., filed Sep. 24, 2013.

Co-pending U.S. Appl. No. 14/007,106, entitled "Method of Using an Absorptive Sensor Element", Pallazzotto et al., filed Sep. 24, 2013.

Co-pending U.S. Appl. No. 14/110,047, entitled "Vapor Sensor Including Sensor Element with Integral Heating", Palazzotto et al., filed Oct. 4, 2013.

Kumazawa, et al, "Novel Method for Gas Sensing Using AC modulated Titanium dioxide thick film sensor-Can we determine a set of concentration in a binary mixture of gases with a single sensor?" The Institute of Electrical Engineers of Japan, Chemical Sensor System Seminar Material, 1998, CS-98-37-47, pp. 7-12.

\* cited by examiner

METHOD OF DETECTING VOLATILE ORGANIC COMPOUNDS

FIELD

The present disclosure relates to methods and device for detection of volatile compounds.

BACKGROUND

The detection of volatile organic compounds (VOCs) is of potential importance in many applications due to environmental and safety concerns. Various methods for VOCs detection have been developed using photoionization, gravimetry, spectroscopy, and so forth. In many current commercialized VOCs detection technologies, VOCs cannot be identified. For example, the popular detection technology, Photo-Ionization Detection (PID), requires prior identification of any VOCs in order to obtain quantitative information. In order to identify VOCs, sophisticated and expensive equipment such as, for example, Gas Chromatography-Mass Spectrometry (GCMS) equipment is generally used. Despite miniaturization efforts, GCMS remains difficult and expensive to use in the field (e.g., in a manufacturing facility or shop).

Various absorptive capacitance sensors or optochemical sensors have been devised that include a dielectric microporous material sandwiched between two layers, at least one of which is porous to analyte vapors (e.g., volatile organic compounds) that become absorbed by the dielectric microporous material. As used herein the term "absorbed" refers to material becoming disposed within the dielectric microporous material, regardless of whether it is merely adsorbed to the pore walls, or dissolved into the bulk dielectric microporous material. These sensors detect changes in properties of the microporous material due to absorbed VOCS. For example, optochemical sensors detect spectral changes in reflected light caused by a change in the index of refraction of the dielectric microporous material, and capacitance sensors detect changes in capacitance caused by a change in dielectric constant of the dielectric microporous material.

SUMMARY

While both optochemical sensors and capacitance sensors have been developed that that are capable of measuring concentration of a known analyte such as a volatile organic compound, until now it has not been known how to using such absorptive sensors to classify analytes by chemical type, much less identify them.

In one aspect, the present disclosure provides a method of using a sensor element, the method comprising the steps:

a) providing a sensor element, the sensor element comprising a reflective conductive electrode, a semi-reflective conductive electrode, and a detection layer comprising dielectric optically-transmissive microporous material sandwiched between the reflective conductive electrode and the semi-reflective conductive electrode, wherein at least one of the semi-reflective conductive electrode or the reflective conductive electrode is permeable to an analyte vapor;

b) determining a baseline capacitance and a baseline reflection spectrum for the sensor element at a temperature and humidity level;

c) obtaining a capacitance of the sensor element while exposed to the analyte vapor to obtain a measured capacitance;

d) obtaining a reflection spectrum of the sensor element while exposed to an analyte vapor to obtain a measured reflection spectrum comprising a spectral feature;

e) obtaining a true capacitance of the sensor element, wherein the true capacitance is equal to the measured capacitance minus a baseline capacitance of the sensor element, f) obtaining a wavelength shift of the spectral feature, wherein the wavelength shift of the spectral feature equals difference in the wavelength of the spectral feature in the baseline reflection spectrum and the measured reflection spectrum;

g) comparing the true capacitance and the wavelength shift of the spectral feature, or at least one derivative thereof, to a reference library, wherein the reference library comprises reference correlations between wavelength shift of the spectral feature and true capacitance, or said at least one derivative thereof, for a plurality of reference analyte vapors;

h) determining at least one of the chemical class or identity of the analyte vapor.

Advantageously, methods according to the present disclosure allows the use of relatively inexpensive and portable vapor sensors (e.g., as compared to GCMS) to classify and/or identify analyte vapors such as for example, volatile organic compounds.

Steps recited in processes of the present disclosure, including the claims, can be carried out in any suitable order, unless otherwise specified.

Sensor elements used in practice of the present disclosure are generally configured such that the absorptive dielectric layer is in sufficiently close proximity to the first conductive electrode and the second conductive electrode that the absorptive dielectric material contained in the layer will be capable of interacting with an electric field that is established by the electrodes. In operation of the sensor element, the absorptive dielectric layer exhibits a change in an electrical property upon absorption of one or more analytes (e.g., one or more organic vapors). The electrical property may be a capacitance-related property as described below. Such a change in a capacitance-related property can be measured by imparting a charge differential between the first conductive electrode and the second conductive electrode (e.g., by imparting a voltage differential to the electrodes) and monitoring the property of the sensor element in response to the presence of the analyte.

The term "capacitance-related property" encompasses any electrical property and the measurement thereof that is in general associated with the imparting of an electrical charge (whether static or time variant) and the monitoring of an electrical property during and/or after the imparting of the charge. Such properties include, for example, not only capacitance, but also impedance, inductance, admittance, current, resistance, conductance, etc., and may be measured according to various methods known in the art.

As used herein:

the term "permeable" in reference to a layer of a material (e.g., a conductive electrode) means that in areas where the layer is present, the layer is sufficiently porous to be non-reactively permeable through its thickness (e.g., at 25° C.) by at least one organic compound;

the term "baseline capacitance" refers to the capacitance that would be observed in the absence of analyte;

the term "true capacitance" refers to the observed capacitance minus the baseline capacitance; and the term "spectral feature" in the context of a reflection spectrum refers to an identifiable feature of the reflection spectrum such as, for example, a peak (a reflection maximum), a valley (reflection minimum), or an inflection point).

The size (intensity) and/or wavelength of spectral feature(s) may change in response to the presence of an analyte. Upon a shift in the position or size of one of more peaks (e.g., due to a change in the concentration of an analyte), the amount, spectral distribution, or intensity of reflected light that is detected by the photodetector may change.

The features and advantages of the present disclosure will be further understood upon consideration of the detailed description as well as the appended claims.

It should be understood that numerous other modifications and embodiments can be devised by those skilled in the art, which fall within the scope and spirit of the principles of the disclosure. The figures may not be drawn to scale. Like reference numbers may have been used throughout the figures to denote like parts.

DETAILED DESCRIPTION

Figure 1:
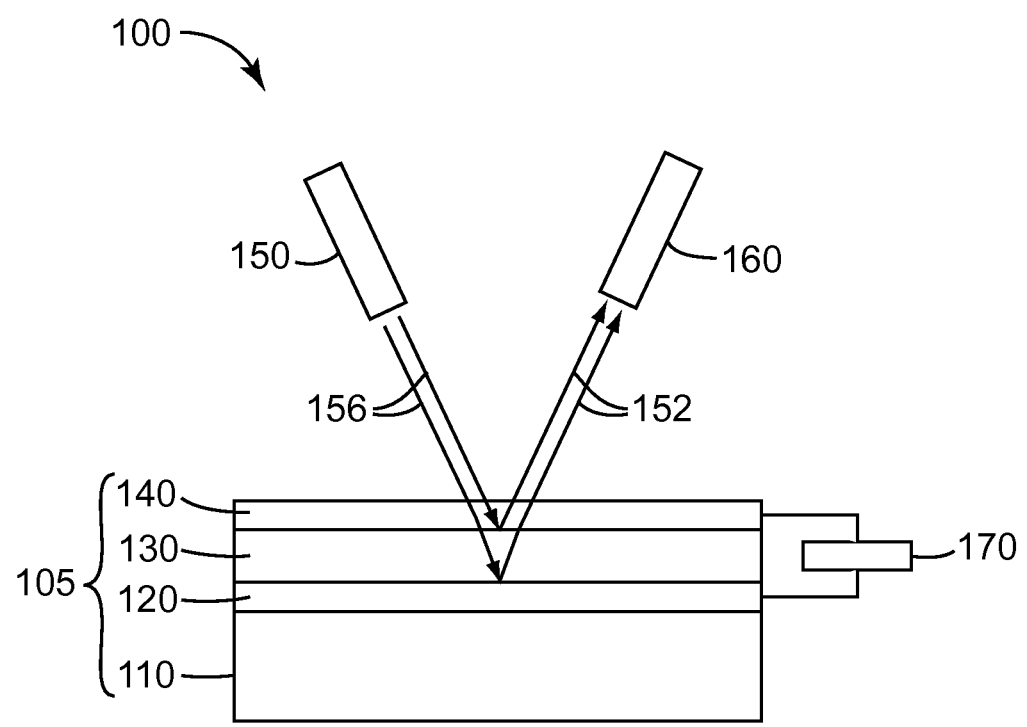
FIG. 1 is schematic cross-sectional view of an exemplary configuration for practicing a method according to the present disclosure.

FIG. 1 illustrates an exemplary configuration for carrying out an exemplary method 100 of detecting volatile organic compounds according to the present disclosure. Referring now to FIG. 1, exemplary sensor element 105 comprises a reflective conductive electrode 120 disposed on optional substrate 110, semi-reflective conductive electrode 140, and detection layer 130 sandwiched between reflective conductive electrode 120 and semi-reflective conductive electrode 140.

Optional substrate 110 may be a continuous slab, layer, or film of material. If present, it is disposed in sufficient proximity to the reflective conductive electrode that it may serve to provide physical strength and integrity to the absorptive sensor element. Any solid dielectric material having structural integrity, flexible or rigid, may be used. Suitable materials include, for example, glass, ceramic, metal, and/or plastic. Desirably, the substrate is dielectric.

Reflective conductive electrode 120 may be made of any material that has a reflective surface. The reflective electrode may be a unitary body, and may be relatively thick or thin. Examples of unitary bodies include reflective metal foils or sheets. Optionally, the reflective conductive electrode may comprise a substrate having a reflective layer disposed thereon, wherein the optional substrate is as defined hereinabove. The reflective conductive electrode material can be tailored to the application. Examples of suitable reflective layers include vapor deposited metals having a thickness of 20 to 200 nanometers (nm), although other thicknesses may also be used. For example, the reflective conductive electrode may have sufficient thickness to be self-supporting (e.g., in a range of from 10 micrometers to one centimeter), although large and lesser thicknesses may also be used. Exemplary suitable materials for the reflective layer include aluminum, chromium, gold, nickel, titanium, palladium, platinum, silicon, silver, and combinations thereof.

Reflective conductive electrode 120 desirably reflects at least 50 percent, 60 percent, 70 percent, 80, or even at least 90 percent, or more of some light that is incident on it within a wavelength range of from 300 nm to 2500 nm, although a lesser reflectivity may also be used.

Detection layer 130 comprises a dielectric optically-transmissive microporous material. In this context, the terms "microporous" and "microporosity" mean that the material has a significant amount of internal, interconnected pore volume, with the mean pore size (as characterized, for example, by sorption isotherm procedures) being less than 100 nm, typically less than 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed.

Examples of suitable dielectric optically-transmissive microporous materials include porous silica and Polymers of Intrinsic Microporosity (PIMs). PIMs are polymeric materials with nanometer-scale pores due to inefficient crystal packing. For example, in *Chemical Communications,* 2004, (2), pp. 230-231, Budd et al. report a series of intrinsically microporous materials containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1 (below).

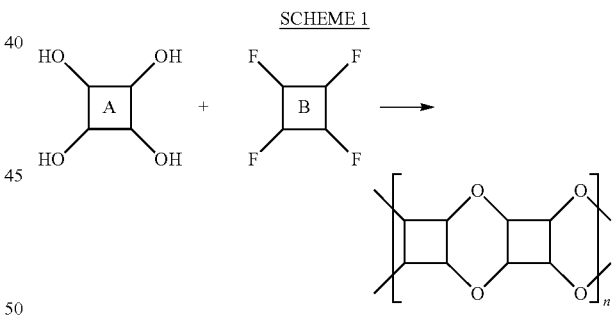

TABLE 1

| COMPONENT A | COMPONENT B |
|---|---|
| A1 | B1 |

TABLE 1-continued

| COMPONENT A | COMPONENT B |
|---|---|
| 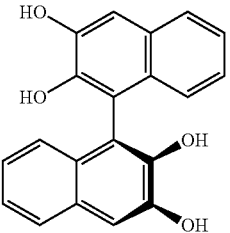 A2 | 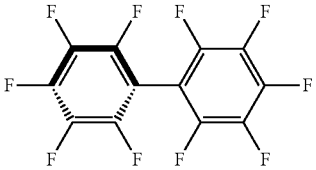 B2 |
| 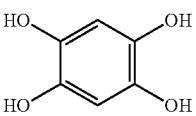 A3 | 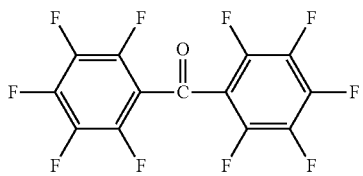 B3 |

Further suitable Components A and B, and resultant intrinsically microporous polymers, are known in the art, for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al. in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Patent Appl. Publ. No. 2006/0246273 (McKeown et al.), the disclosure of which is incorporated herein by reference.

Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state, and thus have at least 10 percent free volume and are intrinsically microporous.

PIMs may be blended with other materials. For example, a PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIM(s) may also be blended with a material that is an absorptive dielectric material (for example, zeolites, activated carbon, silica gel, hyper-crosslinked polymer networks and the like). Such materials may comprise insoluble materials that are suspended in a solution comprising of a PIM material. Coating and drying of such a solution/suspension may provide a composite absorptive dielectric layer comprising both the PIM material and the additional absorptive dielectric material.

PIMs are typically soluble in organic solvents such as, for example, tetrahydrofuran and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film. For example, intrinsically microporous polymers of higher molecular weights may need to be cast from relatively unusual solvents (e.g., cyclohexene oxide, chlorobenzene, or tetrahydropyran) to generate films with desirable properties for use in optochemical sensors as described herein. In addition to solution coating methods, the detection layer may be applied to the reflective substrate by any other suitable method.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

The detection layer may comprise a continuous matrix. Such a matrix is defined as an assembly (e.g., a coating and/or layer) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, or carbon nanotubes). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex or sol-gel layer can be consolidated such that individual particles are no longer discernible, nor is it possible to discern areas of the assembly that were obtained from different particles, such a layer may then be considered to be a continuous matrix.

The semi-reflective conductive electrode is permeable by at least one organic analyte and semi-reflective to visible light; that is, it reflects some incident light (e.g., at least 20, 30, 40, or 50 percent) and transmits (e.g., at least 20, 30, 40, or 50 percent) some incident light over a wavelength range of from 300 nm to 2500 nm, typically over a wavelength range of from 300 nm to 1100 nm. Suitable porous semi-reflective electrodes include, for example, thermal vapor deposited metallic films comprising metals such as copper, silicon, aluminum, rhodium, iridium, nickel, chromium, osmium, gold, silver, palladium, or a combination thereof. In general, the porous semi-reflective conductive electrode may have any thickness as long as it remains semi-reflective. Typically, these properties may be achieved at a thickness of from 1 nm to 50 nm, more typically from 1 nm to 10 nm, and even more typically from 4 nm to 8 nm, although other thickness may also be used. Desired thicknesses will typically depend on the material used to form the electrode, the material onto which the electrode is deposited, the analyte to be detected, and the medium that will carry the analyte. Details concerning vapor-deposited vapor conductive electrodes, suitable for use as semi-reflective conductive electrodes, can also be found in U.S. Provisional Patent Appln. No. 61/388,146 (Palazzotto et al.), the disclosure of which is incorporated herein by reference.

Although the reflective conductive electrode is typically made to be more reflective (e.g., at least 50, 60, 70, 80, 90, 95, or even at least 99 percent reflective) than the semi-reflective conductive electrode, sometimes it is desirable to have the reflectivity of the reflective conductive electrode and semi-reflective conductive electrode be the same; or the permeable conductive electrode can be made reflective and the reflectivity of the other electrode be reduced to make it semi-reflective; for example, so a response to the presence of an analyte can be seen from either side of the sensor film. This can be accomplished for example, by using a conductive ink, composed of silver or gold nanoparticles that can be deposited at a thickness to make the semi-reflective conductive electrode reflective yet still permeable to an analyte. In such a case the permeable electrode can be 50 to 500 nm in thickness.

In some embodiments, the semi-reflective and/or reflective conductive electrode may also be etched or perforated to create holes or other open areas through which analyte can penetrate into the detection layer, although this is not a requirement.

For example, in one embodiment, the reflective conductive electrode is disposed on an optional substrate, and the semi-reflective conductive electrode is permeable to the analyte vapor. In this configuration, a portion of the incident light is directed onto and through the semi-reflective electrode.

In another embodiment, the reflective conductive electrode is permeable to the analyte vapor. Semi-reflective conductive electrode is disposed on an optional substrate, which is optically transmissive to a portion of the incident light. In this configuration, incident light is directed onto and through the optional substrate.

In this implementation, the physical thickness of the detection layer is in a range of from 150 nm to 1200 nm, for example, in a range of from 500 nm to 900 nm, although thinner and thicker detection layers may also be used.

Further details concerning capacitance sensors and optochemical sensors including a microporous polymer, and methods for their manufacture can be found, for example, in PCT International Publication No. WO 2009/045733 A2 (Gryska et al.); and in U.S. Pat. No. 7,556,774 (Rakow et al.) and U.S. Pat. No. 7,556,774 (Rakow et al.), the disclosures of which are incorporated herein by reference.

Upon exposure to an analyte vapor, the dielectric optically-transmissive microporous material absorbs analyte vapor from the environment causing a change in dielectric constant and refractive index of the detection layer. As used herein the term "absorb" refers to material becoming disposed within the dielectric microporous material, regardless of whether it is merely adsorbed to the pore walls, or dissolved into the bulk dielectric microporous material.

Capacitance-related properties of sensor element 105 can be measured, for example, by electrically connecting an impedance analyzer to the reflective conductive electrode 120 and semi-reflective conductive electrode 140. Techniques for capacitance-related property measurement are well known, and accessible to those of skill in the art. This will now be illustrated below in the context of capacitance measurement.

Typically, the sensor element will exhibit a baseline capacitance other than zero, so a baseline capacitance measurement should be taken. The baseline capacitance is defined herein as the capacitance observed under the same conditions (e.g., temperature and humidity), but in the absence of the analyte vapor.

True capacitance is obtained by subtracting the baseline capacitance from the measured capacitance value in the presence of the analyte vapor. In some embodiments, the capacitance may be converted to a relative capacitance, wherein the true capacitance is divided by the true capacitance observed at a known concentration of a known analyte, which may be the same or different than the analyte being measured. Further details concerning relative capacitance can be found in U.S. Provisional Patent Application No. 61/475,014 entitled "ELECTRONIC DEVICE INCLUDING CALIBRATION INFORMATION AND METHOD OF USING THE SAME", filed Apr. 13, 2011, the disclosure of which is incorporated herein by reference.

Optochemical and capacitance measurements may be made at any temperature, however, an elevated temperature in a range of from 30° C. to 100° C., (e.g., in a range of from 40° C. to 80° C., or in a range of from 50° C. to 65° C.), are generally desirable as it tends to minimize effects of humidity and eliminate ambient temperature fluctuations. Heating may be accomplished by any suitable method, including, for example, resistance heater elements. An exemplary configuration wherein the conductive electrode also serves as a heating element is described in U.S. Provisional Patent Application No. 61/475,009 entitled "VAPOR SENSOR INCLUDING SENSOR ELEMENT WITH INTEGRAL HEATING", filed Apr. 13, 2011, the disclosure of which is incorporated herein by reference.

Simultaneously, or sequentially, the semi-reflective conductive electrode is exposed to incident light 156 from light source 150 (e.g., from a tungsten filament bulb, a xenon lamp, a light emitting diode, or a laser) and the reflected light 152 is observed using a photodetector (e.g., a spectrophotometer). Typically, the incident light includes one or more wavelengths in a range of from 300 nm to 2500 nm. The light emitted by the light source may be broad band (e.g., white light) or narrow band (e.g., LED or laser light). The characteristics of the light reflected from the sensor element result from the interference of light that is reflected from various layers (e.g., the reflective conductive electrode and the semi-reflective conductive electrode) and other interfaces of the sensor element. Such reflected light has a reflection spectrum with one or more spectral features (e.g., peaks, valleys, and/or inflection points) over a given wavelength range. The size and/or position of the spectral feature(s) may change in response to the presence of an analyte. Upon a shift in the position or size of one or more wavelength peaks (i.e., due to a change in the concentration of an analyte), the amount, spectral distribution, or intensity of reflected light that is detected by the photodetector may change.

Reflected light is analyzed using a photodetector capable of measuring reflection wavelength maximum band shifts. Reflection wavelength maximum band shifts can be readily obtained, for example, as wavelength shifts in reflection minima (valleys), maxima (peaks), or inflection points. As with capacitance, spectral changes are determined relative to a baseline reflection spectrum observed under identical conditions (e.g., temperature and humidity) in the absence of the analyte.

Further details concerning optochemical measurement techniques and apparatus are described in U.S. Patent Appl. Publ. No. 2010/277740 A1 (Rakow et al.), the disclosure of which is incorporated by reference.

Reference Library

Figure 2:
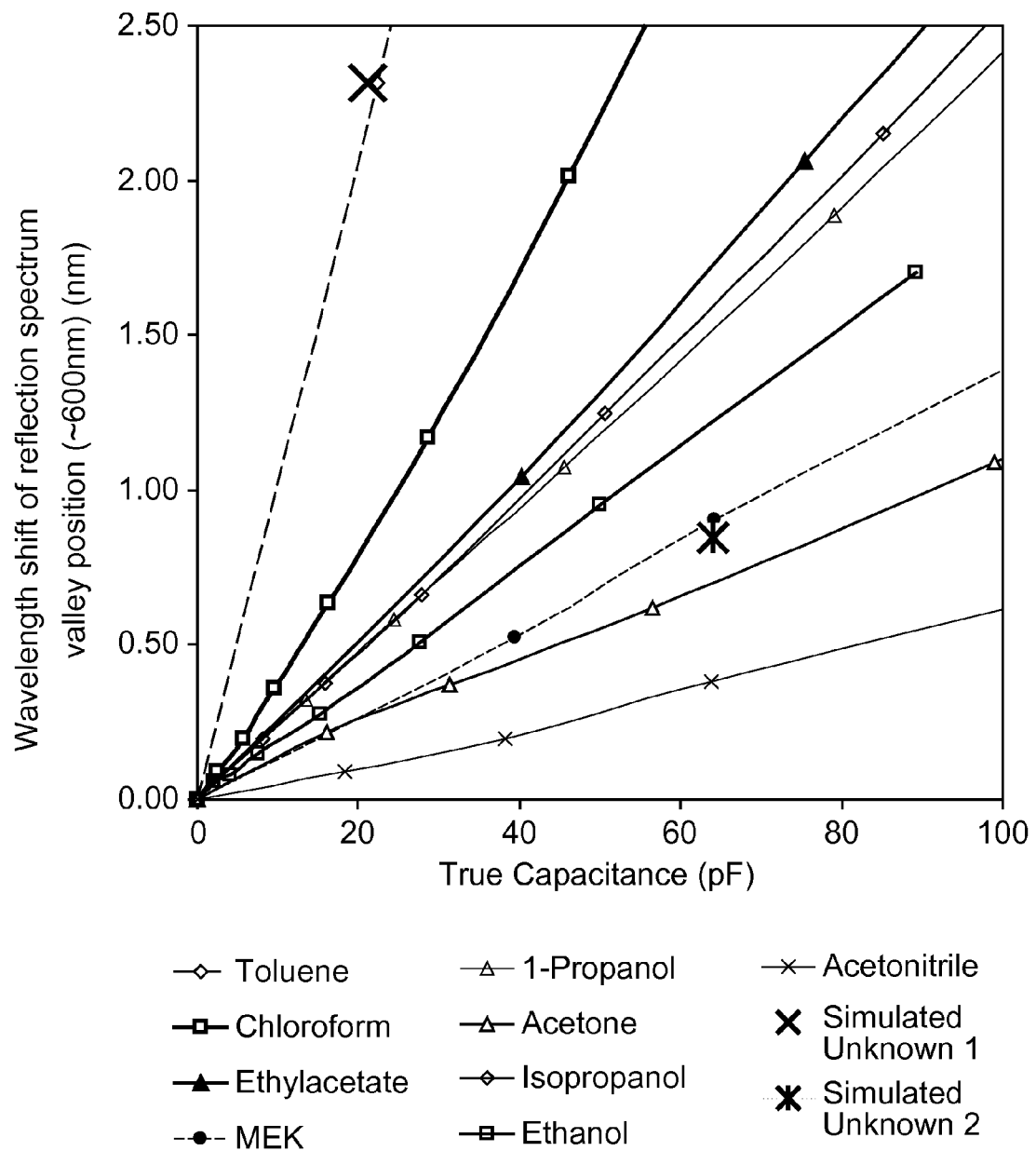
FIG. 2 is a graphical representation of a reference library generated according to Examples 1 and 2.

The reference library comprises a plurality of reference correlations between true capacitance (and/or a derivative thereof) and wavelength shift of at least one spectral feature between the baseline reflection spectrum and measured reflection spectrum. The reference library includes reference correlations, generally made by direct observation as described herein at multiple concentrations of a number of analyte vapors using a sensor element of the substantially the same design and under substantially the same conditions. FIG. 2 shows an exemplary reference library to illustrate the concept.

The reference correlations may comprise, for example, graphs, look up tables, and/or mathematical relationships. In some embodiments, a conversion factor obtained by calibration measurements may need to be applied to the true capacitance in order to obtain the true capacitance and/or spectral change for comparison with the reference library. Details concerning calibration of sensor elements such as those disclosed herein, and comparison with reference correlations can be found, for example, in U.S. Provisional Patent Application No. 61/475,014 entitled "ELECTRONIC DEVICE INCLUDING CALIBRATION INFORMATION AND METHOD OF USING THE SAME", filed Apr. 13, 2011, the disclosure of which is incorporated herein by reference.

Advantageously, it is presently discovered that different classes of VOCs tend to have similar reference correlations, hence depending, for example, on the concentration of the analyte vapor it may be possible to determine the chemical class of an analyte that does not have a corresponding correlation in the reference library. However, the number of commonly encountered VOCs, is relatively small (e.g., from about 40 to 60 VOCs), and it is typical practical to include most or all of them in the reference library.

Examples of common VOCs include ketones (e.g., acetone and 2-(5H)-furanone), aromatic hydrocarbons (e.g., benzene, toluene, ortho-xylene, ethylbenzene, and 4-ethyl-toluene), aliphatic hydrocarbons (e.g., 1,3-butadiene, undecane, limonene, heptanes, nonane, dodecane, hexane, decane, cyclohexane, tetradecane, 1-heptadecene, 1-decene, and octane), halogenated hydrocarbons (e.g., methylene chloride, perchloroethylene, and 1-chlorododecane), alcohols (e.g., ethylene glycol, ethanol, 2-propanol, 2-hydroxymethylfuran, 1-decanol, 2-ethyl-1-hexanol, and phenol), aldehydes (e.g., formaldehyde, acetaldehyde, and hexanal), carboxylic acids (e.g., acetic acid, hexadecanoic acid, dodecanoic acid, nonanoic acid, 1-dodecene, and octadecanoic acid), lactams (e.g., N-methylpyrrolidone), esters (e.g., ethyl acetate, butyl acetate, and bis(2-ethylhexyl) phthalate), ethers (e.g., 2-pentylfuran), cyclopentasiloxane, and carbon disulfide.

In comparing measured spectral change and capacitance values (i.e., measured parameters) to the reference library, it is self-evident that the reference correlations should be between parameters measured using the sensor element (e.g., wavelength shift as a function of true capacitance, or color change as a function of relative capacitance).

Comparison between the measured parameters and the reference correlations may be done graphically, or by a mathematical algorithm such as, for example, minimization of the residuals between the measured parameters and the reference parameters. Such methods are well-known in the art.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Preparation of PIM Material

A PIM (Polymer of Intrinsic Microporosity) was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459. 5,5',6,6'-tetrahydroxy-3,3,3',3'-tetramethyl-1,1'-spirobisindane (100.00 grams (g)) were combined with 59.219 g of tetrafluoroterephthalonitrile, 243.6 g potassium carbonate, and 2543.6 g of N,N-dimethylformamide, and the mixture was reacted at 68° C. for 72 hours. The polymerization mixture was poured into water, and the precipitate was isolated by vacuum filtration. The resulting polymer was twice dissolved in tetrahydrofuran, precipitated from ethanol, and air dried at room temperature. A yellow solid product was obtained having a number-average molecular weight of approximately 40800 g/mol, as determined by gel permeation chromatography analysis using light scattering detection.

Method for Sensor Element Preparation

Sensor elements were prepared on PGO glass slides (glass number 0050-0050-0010-GF-CA, 50 mm×50 mm, 1.1 mm thick, material C-263, surface 80/50, obtained from Precision Glass & Optics of Santa Ana, Calif.), which were cleaned by soaking them in LIQUI-NOX detergent solution (obtained from Alconox, Inc. of White Plains, N.Y.) for 30 to 60 minutes, then scrubbing each side of the slides with a bristle brush, rinsing them under warm tap water followed by a final rinse with deionized water (DI water). The slides were allowed to air dry covered to prevent dust accumulation on the surface. The dry, clean slides were stored in 7.6 cm (3 inch) wafer carriers obtained from Entegris of Chaska, Minn.

A reflective conductive electrode was deposited onto the PGO glass slide by thermally vapor coating 5.0 nm of titanium (obtained as titanium slug, 9.5 mm×9.5 mm, 99.9+% purity from Alfa Aesar, Ward Hill, Mass.) at a rate of 0.1 nm per second (nm/sec) followed by 100.0 nm of nickel (obtained as 3.175 mm×3.175 mm slug, 99.995% pure from Alfa Aesar) at 0.1 nm/sec using a square mask (MASK A) having a single rectangular opening with a top border of 0.46 inch (1.2 cm), a bottom border of 0.59 inch (1.5 cm), and left and right borders of 0.14 inch (0.35 cm) prepared from laser-cut 1.16 mm thick stainless steel. The deposition process was controlled using an INFICON XTC/2 THIN FILM DEPOSITION CONTROLLER from INFICON of East Syracuse, N.Y.

A PIM solution of 4.0 percent by weight in chlorobenzene was prepared by mixing the components in a small jar and placing it on a roller mill (Mini Bottle Roller number 348920 from Wheaton Science Products, Millville, N.J.) for about 3 hours then filtering through an ACRODISC 25 MM SYRINGE FILTER WITH 1 MICRON GLASS FIBER MEMBRANE filter disk from PALL Life Sciences, Ann Arbor, Mich. The solution was allowed to sit over night so that any bubbles that formed could escape.

Samples were spin-coated with PIMS using a Model WS 400B-8NPP/LITE spin coater from Laurell Technologies Corporation of North Wales, Pa. To coat a sample, it was placed in the spin coater and about 0.5 ml of chlorobenzene was placed on the sample. Each sample was spun 60 seconds at 1000 rpm after the chlorobenzene was applied. Then, for all samples, the PIMS solution was dispensed and coated in the same manner. After spin coating, PIMS thickness measurements were made using a Model XP-1 profilometer from AMBiOS Technology of Santa Cruz, Calif. by removing a small section of the coating with an acetone soaked cotton swab. The parameters used in the thickness measurement were a scan speed of 0.1 mm/sec, a scan length of 5 mm, a range of 10 micrometers, a stylus force of 0.20 mg and a filter level of 4. All samples were baked for 1 hour at 100° C. after coating. The thickness of PIMS layer was 745 nm.

A 2 inches (5 cm)×2 inches (5 cm) mask (MASK B) having a 2×2 regular array of four 0.60 inch (1.5 cm) height×0.33 inch (0.84 cm) width rectangular openings vertically separated by 0.22 inch (0.56 cm) and horizontally separated by 0.48 inch (1.2 cm) was made from 24 gauge stainless steel by laser milling. The semi-reflective conductive electrode was vapor deposited through the semi-reflective conductive electrode mask using thermal deposition of gold (obtained as metal spatters, 99.999% typical purity from Cerac Inc., Milwaukee, Wis.) at various thicknesses. A deposition rate of 0.1 nm/sec was used for 6 nm. After depositing the semi-reflective conductive electrode, a connecting electrode (to facilitate electrical contact for testing) was deposited by thermally vapor coating 5.0 nm of titanium (obtained as titanium slug, 9.5 mm×9.5 mm, 99.9+% purity from Alfa Aesar) at a rate of 0.1 nm/sec followed by 100.0 nm of nickel (obtained as 3.175 mm×3.175 mm slug, 99.995% pure from Alfa Aesar) at 0.5 nm/sec through a 2 inches (5 cm)×2 inches (5 cm) mask (MASK C) having two horizontal rectangular openings with a height of 0.4 inch (1 cm), left and right borders of 0.14 inch (0.36 cm), and a separation of 0.92 inch (2.4 cm), prepared by laser milling from 50 gauge stainless. The deposition process was controlled using an INFICON XTC/2 THIN FILM DEPOSITION CONTROLLER.

This sensor element production process produced a sensor element of approximately 10 mm×9 mm active area (area under the overlapping semi-reflective conductive electrode and reflective conductive electrode that was not covered by the connecting electrode) on an approximately 25 mm×25 mm glass substrate.

Capacitance Measurement Method

Before testing, the sensor element was baked at 180° C. for 30 min using a convection oven. All tests were performed in air that had been passed over DRIERITE dessicant (W. A. Hammond Drierite Co. Ltd., Xenia, Ohio) to remove moisture, and passed over activated carbon to eliminate any organic contaminates. The testing chamber allowed the measurement of four sensor specimens at a time. Vapor tests were conducted using a 10 L/minute dry air flow through the system. Various vapor levels were generated using a KD Scientific syringe pump (available from KD Scientific Inc. of Holliston, Mass.) fitted with a 500-microliter gas tight syringe (obtained from Hamilton Company of Reno, Nev.). The syringe pump delivered the organic liquid onto a piece of filter paper suspended in a 500 ml three necked flask. The flow of dry air pass the paper vaporized the solvent. Delivering the solvent at different rates by controlling the syringe pump generated different concentrations of vapor. The syringe pump was controlled by a LABVIEW (software available from National Instruments of Austin, Tex.) program that allowed vapor profiles to be generated during a test run. A MIRAN IR analyzer (available from Thermo Fischer Scientific, Inc. of Waltham, Mass.) was used to verify the set concentrations. The capacitance and dissipation factors were measured with an Agilent LCR meter (model E4980A Precision LCR Meter from Agilent Technologies, Inc., Santa Clara, Calif.) applying one volt at 1000 Hz across the semi-reflective conductive electrode and reflective conductive electrode. The temperature of sensors was controlled using flexible heaters, thermocouples, and a feedback-loop controlling program. The flexible heaters (available from Omega Engineering, Inc) were located underneath aluminum plates and thermocouples were located between aluminum plates and flexible heaters. The sensors were placed on the aluminum plates. The actual temperature on the sensors was calibrated using thermocouples on the sensors and thermocouples under the aluminum plates. The operating temperature was 55° C. The capacitance data were collected and stored using the same LABVIEW program that controlled the syringe pump and temperature.

Optoelectronic Measurement Method

Wavelength shifts of valleys (i.e., minima) in the reflection spectrum were determined using a reflection spectroscopy system (available from Ocean Optics, Model Jaz). The reflection optical probe was located above 10 mm×9 mm active area of the capacitor configuration. Reflection spectrum valley positions located at about 600 nm were used to measure wavelength shift.

Example 1

Simultaneous capacitance and optoelectronic measurements at various concentrations with various VOC vapors using a sensor element prepared as described in the Method for Sensor Element Preparation were made according to the respective methods above. Results are reported in Tables 2-10 (below), wherein the reflection spectrum valley wavelength shift refers to a valley in the reflection spectrum occurring at about 600 nm.

TABLE 2

ETHYL ACETATE

| CONCENTRATION, parts per million (ppm) | TRUE CAPACITANCE, picofarads (pF) | REFLECTION SPECTRUM VALLEY WAVELENGTH SHIFT, nm |
|---|---|---|
| 0 | 0 | 0.00 |
| 15 | 40.2 | 1.04 |
| 30 | 75.46 | 2.06 |
| 60 | 121.76 | 3.46 |
| 125 | 181.67 | 5.44 |
| 250 | 248.47 | 7.85 |
| 500 | 326.36 | 11.11 |
| 1000 | 399.81 | 14.92 |

TABLE 3

ISOPROPANOL

| CONCENTRATION, ppm | TRUE CAPACITANCE, pF | REFLECTION SPECTRUM VALLEY WAVELENGTH SHIFT, nm |
|---|---|---|
| 0 | 0 | 0.00 |
| 15 | 8.12 | 0.19 |
| 30 | 15.91 | 0.37 |
| 60 | 27.92 | 0.66 |
| 125 | 50.53 | 1.25 |
| 250 | 85.26 | 2.15 |
| 500 | 133.28 | 3.50 |
| 1000 | 203.37 | 5.51 |

TABLE 4

ETHANOL

| CONCENTRATION, ppm | TRUE CAPACITANCE, pF | REFLECTION SPECTRUM VALLEY WAVELENGTH SHIFT, nm |
|---|---|---|
| 0 | 0 | 0.00 |
| 15 | 1.99 | 0.06 |
| 30 | 4.09 | 0.08 |
| 60 | 7.58 | 0.15 |
| 125 | 15.27 | 0.27 |
| 250 | 27.6 | 0.51 |
| 500 | 49.92 | 0.95 |
| 1000 | 89.2 | 1.70 |

TABLE 5

CHLOROFORM

| CONCENTRATION, ppm | TRUE CAPACITANCE, pF | REFLECTION SPECTRUM VALLEY WAVELENGTH SHIFT, nm |
|---|---|---|
| 0 | 0 | 0.00 |
| 3 | 2.38 | 0.09 |
| 6 | 5.62 | 0.20 |
| 10 | 9.64 | 0.36 |
| 20 | 16.17 | 0.63 |
| 40 | 28.62 | 1.17 |
| 80 | 46.04 | 2.01 |
| 160 | 72.45 | 3.37 |

TABLE 6

ACETONE

| CONCENTRATION, ppm | TRUE CAPACITANCE, pF | REFLECTION SPECTRUM VALLEY WAVELENGTH SHIFT, nm |
|---|---|---|
| 0 | 0 | 0.00 |
| 15 | 16.07 | 0.22 |
| 30 | 31.22 | 0.37 |
| 60 | 56.6 | 0.62 |
| 125 | 99 | 1.09 |
| 250 | 164.51 | 1.86 |
| 500 | 252.25 | 2.98 |
| 1000 | 381.02 | 4.72 |

TABLE 7

1-PROPANOL

| CONCENTRATION, ppm | TRUE CAPACITANCE, pF | REFLECTION SPECTRUM VALLEY WAVELENGTH SHIFT, nm |
|---|---|---|
| 0 | 0 | 0.00 |
| 15 | 13.42 | 0.32 |
| 30 | 24.32 | 0.58 |
| 60 | 45.49 | 1.07 |
| 125 | 79 | 1.89 |
| 250 | 130.18 | 3.20 |
| 500 | 204.39 | 5.19 |
| 1000 | 312.98 | 8.28 |

TABLE 8

METHYL ETHYL KETONE

| CONCENTRATION, ppm | TRUE CAPACITANCE, pF | REFLECTION SPECTRUM VALLEY WAVELENGTH SHIFT, nm |
|---|---|---|
| 0 | 0 | 0.00 |
| 6 | 39.52 | 0.52 |
| 12 | 64.26 | 0.90 |
| 25 | 115.21 | 1.61 |
| 50 | 185.62 | 2.70 |
| 100 | 272.08 | 4.15 |
| 200 | 395.6 | 6.41 |
| 400 | 532.29 | 9.18 |

TABLE 9

ACETONITRILE

| CONCENTRATION, ppm | TRUE CAPACITANCE, pF | REFLECTION SPECTRUM VALLEY WAVELENGTH SHIFT, nm |
|---|---|---|
| 0 | 0 | 0.00 |
| 20 | 18.2 | 0.09 |
| 40 | 38.23 | 0.19 |
| 80 | 63.88 | 0.38 |
| 160 | 108.06 | 0.66 |

TABLE 10

| | TOLUENE | |
|---|---|---|
| CONCENTRATION, ppm | TRUE CAPACITANCE, pF | REFLECTION SPECTRUM VALLEY WAVELENGTH SHIFT, nm |
| 0 | 0 | 0.00 |
| 3 | 22.40 | 2.32 |
| 6 | 36.87 | 4.08 |
| 12 | 51.54 | 5.76 |
| 25 | 71.7 | 8.54 |
| 50 | 91.06 | 11.88 |
| 100 | 110.46 | 16.24 |
| 200 | 124.06 | 21.11 |

Example 2

Three months after completing the capacitance and optoelectronic response measurements in Example 1, the same sensor element was exposed to two simulated unknown VOC vapors. One was toluene (3 ppm) and the other was methyl ethyl ketone (MEK, 12 ppm). Table 11 (below) reports results obtained from simultaneous capacitance and optoelectronic measurements according to the methods used in Example 1.

TABLE 11

| SIMULATED UNKNOWN | ACTUAL VAPOR COMPOSITION | TRUE CAPACITANCE, pF | REFLECTION SPECTRUM VALLEY WAVELENGTH SHIFT, nm |
|---|---|---|---|
| 1 | Toluene, 3 ppm | 21.21 | 2.32 |
| 2 | MEK, 12 ppm | 64.11 | 0.85 |

FIG. 2 shows, in graphical format, reference correlations between spectral change and true capacitance obtained from Example 1, and the observed measurement from Simulated Unknowns 1 and 2 in Table 11. The measurements of Simulated Unknown 1 were compared with the toluene reference correlation, and those of Simulated Unknown 2 with the MEK reference correlation. In FIG. 2, the position of Simulated Unknown 1 corresponds closely to expected values based on the reference correlation for toluene, and Simulated Unknown 2 corresponds closely to expected values based on the reference correlation for MEK.

Various modifications and alterations of this disclosure may be made by those skilled in the art without departing from the scope and spirit of this disclosure, and it should be understood that this disclosure is not to be unduly limited to the illustrative embodiments set forth herein.

Select Embodiments of the Present Disclosure

In a first embodiment, the present disclosure provides a method of using a sensor element, the method comprising the steps:

a) providing a sensor element, the sensor element comprising a reflective conductive electrode, a semi-reflective conductive electrode, and a detection layer comprising dielectric optically-transmissive microporous material sandwiched between the reflective conductive electrode and the semi-reflective conductive electrode, wherein at least one of the semi-reflective conductive electrode or the reflective conductive electrode is permeable to an analyte vapor;

b) determining a baseline capacitance and a baseline reflection spectrum for the sensor element at a temperature and humidity level;

c) obtaining a capacitance of the sensor element while exposed to the analyte vapor to obtain a measured capacitance;

d) obtaining a reflection spectrum of the sensor element while exposed to an analyte vapor to obtain a measured reflection spectrum comprising a spectral feature;

e) obtaining a true capacitance of the sensor element, wherein the true capacitance is equal to the measured capacitance minus a baseline capacitance of the sensor element, f) obtaining a wavelength shift of the spectral feature, wherein the wavelength shift of the spectral feature equals difference in the wavelength of the spectral feature in the baseline reflection spectrum and the measured reflection spectrum;

g) comparing the true capacitance and the wavelength shift of the spectral feature, or at least one derivative thereof, to a reference library, wherein the reference library comprises reference correlations between wavelength shift of the spectral feature and true capacitance, or said at least one derivative thereof, for a plurality of reference analyte vapors;

h) determining at least one of the chemical class or identity of the analyte vapor.

In a second embodiment, the present disclosure provides a method according to the first embodiment, wherein steps d) and e) are simultaneous.

In a third embodiment, the present disclosure provides a method according to the first or second embodiment, wherein the dielectric optically-transmissive microporous material comprises a polymer of intrinsic microporosity.

In a fourth embodiment, the present disclosure provides a method according to any one of the first to third embodiments, wherein step h) comprises determining the chemical class of the analyte vapor.

In a fifth embodiment, the present disclosure provides a method according to any one of the first to fourth embodiments, wherein step h) comprises determining the identity of the analyte vapor.

In a sixth embodiment, the present disclosure provides a method according to any one of the first to fifth embodiments, wherein the analyte vapor comprises an organic compound.

In a seventh embodiment, the present disclosure provides a method according to any one of the first to sixth embodiments, wherein the reflective conductive electrode is disposed on a substrate.

In an eighth embodiment, the present disclosure provides a method according to the seventh embodiment, wherein the substrate is dielectric.

What is claimed is:

1. A method of using a sensor element, the method comprising the steps:

a) providing a sensor element, the sensor element comprising a reflective conductive electrode, a semi-reflective conductive electrode, and a detection layer comprising dielectric optically-transmissive microporous material sandwiched between the reflective conductive electrode and the semi-reflective conductive electrode, wherein at least one of the semi-reflective conductive electrode or the reflective conductive electrode is permeable to an analyte vapor;

b) determining a baseline capacitance and a baseline reflection spectrum for the sensor element at a temperature and humidity level;
c) obtaining a capacitance of the sensor element while exposed to the analyte vapor to obtain a measured capacitance;
d) obtaining a reflection spectrum of the sensor element while exposed to an analyte vapor to obtain a measured reflection spectrum comprising a spectral feature;
e) obtaining a true capacitance of the sensor element, wherein the true capacitance is equal to the measured capacitance minus a baseline capacitance of the sensor element;
f) obtaining a wavelength shift of the spectral feature, wherein the wavelength shift of the spectral feature equals difference in the wavelength of the spectral feature in the baseline reflection spectrum and the measured reflection spectrum;
g) comparing a pairing of the true capacitance and the wavelength shift to a reference library, wherein the reference library comprises reference correlations between the wavelength shift and the true capacitance, or at least one derivative thereof, for a plurality of reference analyte vapors; and
h) determining at least one of the chemical class or identity of the analyte vapor based on the comparison of step g), wherein steps d) and e) are simultaneous.

2. The method of claim 1, wherein the dielectric optically-transmissive microporous material comprises a polymer of intrinsic microporosity.

3. The method of claim 1, wherein step h) comprises determining the chemical class of the analyte vapor.

4. The method of claim 1, wherein step h) comprises determining the identity of the analyte vapor.

5. The method of claim 1, wherein the analyte vapor comprises an organic compound.

6. The method of claim 1, wherein the reflective conductive electrode is disposed on a substrate.

7. The method of claim 6, wherein the substrate is dielectric.

* * * * *